United States Patent [19]

Eichhorn et al.

[11] Patent Number: 5,612,169
[45] Date of Patent: Mar. 18, 1997

[54] N,N-DISUBSTITUTED SULFONAMIDES AND RADIATION-SENSITIVE MIXTURE PREPARED THEREWITH

[75] Inventors: Mathias Eichhorn, Niedernhausen; Gerhard Buhr, Koenigstein, both of Germany

[73] Assignee: Hoechst Aktiengesellschaft, Frankfurt am Main, Germany

[21] Appl. No.: 287,054

[22] Filed: Aug. 8, 1994

Related U.S. Application Data

[62] Division of Ser. No. 165,132, Dec. 10, 1993, abandoned.

[30] Foreign Application Priority Data

Dec. 14, 1992 [DE] Germany .......................... 42 42 051.2

[51] Int. Cl.$^6$ .......................... G03C 1/492; G03C 1/494; G03C 1/76; G03C 1/725
[52] U.S. Cl. .......................... 430/270.1; 430/281.1; 430/326
[58] Field of Search .......................... 430/270, 326, 430/270.1, 281.1

[56] References Cited

U.S. PATENT DOCUMENTS

| | | | |
|---|---|---|---|
| 3,779,778 | 12/1973 | Smith et al. | 96/115 R |
| 3,933,894 | 1/1976 | Stephens | 260/470 |

(List continued on next page.)

FOREIGN PATENT DOCUMENTS

| | | | |
|---|---|---|---|
| 0102450 | 3/1984 | European Pat. Off. | G03F 7/08 |
| 0249139 | 12/1987 | European Pat. Off. | G03F 7/10 |
| 0366590 | 5/1990 | European Pat. Off. | G03F 7/39 |
| 394191 | 10/1990 | European Pat. Off. | |
| 0421388 | 4/1991 | European Pat. Off. | |
| 2407668 | 6/1979 | France. | |
| 64-003162 | 1/1989 | Japan. | |

OTHER PUBLICATIONS

Grant & Hackh's Chemical Dictionary, Grant, ed., 5th Ed., pp. xi, 282, 403–404, 1987.
Acta Chemica Scandina Vica, Series B–Organic Chemistry and Biochemistry, BD. 40, NR. 9, 1986, Copenhagen, DK, pp. 745–750, L. Grehn et al.: "A Simple Method for Tert–Butoxycarbonylation of Amides", Verbindung 21.
Tetrahedron Letters, BD. 30, NR. 42, 1989, Oxford, GB, pp. 5709–5712, J.E. Henry et al.: "Mitsunobu Reactions of N–Alkyl and N–Acyl Sulphonamides – An Efficient Route to Protected Amines", Tabelle 2, 2. Spalte, Zeilen 1, 2.
Journal of Medicinal Chemistry, BD. 35, NR. 20, Oct. 2, 1992, Washington, D.C., pp. 3641–3647, M.J.C. Lee et al.: "N–Hydroxylated Derivatives of Chlorpropamide and its Analogues as Inhibitors of Aldehyde Dehydrogenase in Vivo", Verbindungen 10B, 11B, 12B.
Journal of Medicinal Chemistry, BD. 32, NR. 6, Jun. 1989, Washington, D. C., pp. 1335–1340, H. T. Nagasawa et al.: "N1–Alkyl Substituted Derivatives of Chlorpropamide as Inhibitors of Aldehyde Dehydrogenase", Verbindung 5.

Synthetic Communications, BD. 20, NR. 14, 1990, New York, pp. 2083–2090, I. Atanasova et al.: "Alpha,Alpha, Alpha–Trichlormethylcarbonyl Compounds as Acylating Reagents of Amides", Verbindung 3K.
Chemical Abstracts, vol. 102, No. 13, Apr. 1, 1985, Columbus, Ohio, Abstract No. 113079A, p. 672; and JP–A–59 204 165 (Sumitomo Chemical), Nov. 19, 1984 Zusammenfassung.
Chemical Abstracts, vol. 93, No. 19, Nov. 10, 1980, Columbus, Ohio; Abstract No. 181032A, p. 191; and JP–A–50 089 208 (Nippon Soda), Jul. 5, 1980 Zusammenfassung.
Chemical Abstracts, vol. 91, No. 25, Dec. 17, 1979, Columbus, Ohio, Abstract No. 211082V, p. 651; and JP–A–54 061 148 (Nippon Soda), May 17, 1979 Zusammenfassung.
Chemical Abstracts, vol. 84, No. 25, Jun. 21, 1976, Columbus, Ohio, Abstract No. 175167W, P. 176; and JP–A–51 015 321 (Ube Industries), Feb. 7, 1976 Zusammenfassung.
Chemical Abstracts, vol. 88, No. 7, Feb. 13, 1978, Columbus, Ohio, Abstract No. 46376X, p. 179; and JP–A–52 070 020 (Hokko Chemical Industry), Jun. 10, 1977 Zusammenfassung.
Chemical Abstracts, vol. 72, No. 15, Apr. 13, 1970, Columbus, Ohio, Abstract No. 78623M, L. P. Glushko et al.: "Sulphanilides. XXIII. Isopropyl Esters of N–Arylsulphonyl–N–Phenylcarbamic Acids", p. 356; and Isv. Vyssh. Ucheb. Zaved., Khim. Khim. Teknol., 1969, 12(10), 1373 1374.
Chemical Abstracts, vol. 111, No. –(1989); Abstract No. 111.77653h: "Preparation of Sulfonamide Derivatives as Bactericides and Fungicides"; and JP 64 03, 162.
Chemical Abstracts, vol. 114, No. –(1991); Abstract No. 114:1850406: "Preparation of Sulfenylated Carbamates as Insecticides"; and EP 394,191.

Primary Examiner—George F. Lesmes
Assistant Examiner—Bernard P. Codd
Attorney, Agent, or Firm—John M. Genova

[57] ABSTRACT

The invention relates to N,N-disubstituted sulfonamides of the formulae $R^1[-N(CO-OR^2)-SO_2-R^3]_n$ (I) and $R^1[-SO_2-N(CO-OR^2)-R^3]_n$ (II), in which $R^1$—for n=1—is a $(C_1-C_{20})$alkyl, $(C_3-C_{10})$cycloalkyl, $(C_6-C_{14})$ aryl or $(C_7-C_{20})$aralkyl radical, for n>1—the 2-, 3- or 4-valent radical of a $(C_1-C_{20})$alkane or $(C_6-C_7)$cycloalkane, a noncondensed or condensed mono- or polynuclear $(C_6-C_{18})$aromatic compound, $R^2$ is a $(C_3-C_{11})$alkyl, $(C_3-C_{11})$alkenyl or $(C_7-C_{11})$aralkyl radical, $R^3$ is an unsubstituted or substituted $(C_1-C_6)$alkyl, $(C_3-C_6)$cycloalkyl, $(C_6-C_{14})$aryl or $(C_7-C_{20})$aralkyl radical. The invention further relates to a positive radiation-sensitive mixture containing a) a compound which under the influence of actinic radiation forms acid, b) an acid-cleavable compound whose cleavage products in an aqueous alkaline developer have a higher solubility than the starting compound, and c) a polymeric binder which is insoluble in water but is soluble or at least swellable in aqueous alkaline solutions, in which the compound b) is a sulfonamide of the formula I or II. The mixture according to the invention is particularly suitable for the manufacture of offset printing plates and photoresists.

8 Claims, No Drawings

U.S. PATENT DOCUMENTS

| | | | |
|---|---|---|---|
| 3,971,650 | 7/1976 | Schinski | 71/103 |
| 4,101,323 | 7/1978 | Buhr et al. | 96/35 |
| 4,247,611 | 1/1981 | Sander et al. | 430/286 |
| 4,248,957 | 2/1981 | Sander et al. | 430/270 |
| 4,250,247 | 2/1981 | Sander et al. | 430/270 |
| 4,311,782 | 1/1982 | Buhr et al. | 430/270 |
| 4,602,263 | 7/1986 | Borror et al. | 430/348 X |
| 5,229,254 | 7/1993 | Lohaus et al. | 430/326 X |
| 5,529,886 | 6/1996 | Eichhorn et al. | 430/270.1 |

N,N-DISUBSTITUTED SULFONAMIDES AND RADIATION-SENSITIVE MIXTURE PREPARED THEREWITH

This is a divisional of copending application Ser. No. 08/165,132 filed on Dec. 10, 1993, now abandoned.

DESCRIPTION

The invention relates to N,N-disubstituted sulfonamides and a positive radiation-sensitive mixture which contains:

a) a compound which under the influence of actinic radiation forms acid, b) an acid-clearable compound whose cleavage products in an aqueous-alkaline developer have a higher solubility than the starting compound, and c) a polymeric binder which is insoluble in water but is soluble or at least swellable in aqueous alkaline solutions.

It is particularly suitable for a recording material comprising a base and a radiation-sensitive layer for preparing offset printing plates and photoresists.

Positive radiation-sensitive recording layers, i.e. layers whose solubility is greater in the irradiated zones than in the non-irradiated ones, are known. As the photosensitive component in such layers, ortho-naphthoquinone diazides in particular have gained general acceptance. The photosensitivity of these layers is usually unsatisfactory, however.

The so-called "chemically enhanced" mixtures in comparison show a higher photosensitivity, as the quantum yield is greater than 1. Positive "chemically enhanced" mixtures as a rule contain an acid-forming and an acid-cleavable component, whose cleavage products in aqueous alkaline developers have a greater solubility than the initial compound.

The acid-cleavable compounds used hitherto were monomeric and polymeric acetals and O,N— acetals which as the hydroxyl or amino component contain aromatic compounds (U.S. Pat. No. 3,779,778) and orthoesters and amide acetals (DE-B 26 10 842). Radiation-sensitive positive mixtures are also obtained when employing polymeric orthoesters (EP-B 0 022 571), polymeric aliphatic acetals (DE-A 27 18 254), enol ethers (EP-B 0 006 627) and N-acyliminocarbonates (EP-B 0 006 626). Mixtures of this type, in order to initiate the cleavage reaction, require not only the photochemically generated acid, but also water, which leads to problems in practical applications. Furthermore, many of these compounds are not readily accessible.

A positive radiation-sensitive mixture which contains a compound which upon irradiation produces acid, and also contains a polymer having pendent, acid-labile t-butoxycarbonyl or t-butoxycarbonyloxy groups, is described in EP-A 0 102 450 and in EP-A 0 366 590. A similar mixture, which, however, instead of said polymers contains low-molecular weight compounds having acid-labile groups is disclosed in EP-A 0 249 139. Disclosed as acid-labile groups in the low-molecular weight compounds which generally have a molecular weight of less than 1000 are, in particular, t-butoxy, t-butoxycarbonyl, t-butoxycarbonyloxy, 1-methyl-1-phenylethoxycarbonyl and trimethylsilanyloxy groups. While such systems do not require water for initiating the cleavage reaction, they are not devoid of drawbacks either: for example, they show relatively high "dark ablation", i.e. the solubility of the radiation-sensitive layer in a developer is relatively high even in the unexposed zones, which results in poor differentiation between exposed and unexposed zones.

The object of the invention is to provide acid-cleavable compounds which are particularly suitable for a positive mixture having a high sensitivity for actinic radiation, especially short-wavelength actinic radiation and at the same time can be prepared simply and inexpensively.

This object is achieved according to the invention by providing N,N-disubstituted sulfonamides of the formulae $R^1[-N(CO-OR^2)-SO_2-R^3]_n$ (I) or $R^1[-SO_2-N(CO-OR^2)-R^3]_n$ (II), in which $R^1$ for n=1 is a $(C_1-C_{20})$alkyl, $(C_3-C_{10})$cycloalkyl, $(C_6-C_{14})$aryl or $(C_7-C_{20})$aralkyl radical, individual methylene groups in the radicals containing alkyl being optionally replaced by heteroatoms, for n=2, 3 or 4 is the n-valent radical of a $(C_1-C_{20})$alkane or $(C_5-C_7)$cycloalkane, individual methylene groups in the n-valent $(C_3-C_{20})$alkane radicals being optionally replaced by heteroatoms, by $(C_5-C_7)$cycloalkylene radicals or by phenylene, or the n-valent radical of a noncondensed or condensed mono- or polynuclear $(C_6-C_{18})$aromatic compound, $R^2$ is a $(C_3-C_{11})$alkyl, $(C_3-C_{11})$alkenyl or $(C_7-C_{11})$aralkyl radical, $R^3$ is an unsubstituted or substituted $(C_1-C_6)$alkyl, $(C_3-C_6)$cycloalkyl, $(C_6-C_{14})$aryl or $(C_7-C_{20})$aralkyl radical, and n is an integer from 1 to 4.

In the radical $R^1$, preferably no more than three methylene groups are replaced by heteroatoms, cycloalkylene and/or phenylene. A possible heteroatom is, in particular, oxygen. Compounds with n=1 or 2 are generally preferred. For n=2 a preferred radical $R^1$ has the formula -A-X-B-, in which X is a C—C single bond, a methylene group or an oxygen atom, and A and B, independently of one another, are arylene, in particular ortho-, meta-or para-phenylene, or cycloalkanediyl, in particular cyclohexanediyl.

The compounds according to the invention of the formulae I or II can be prepared from N-monosubstituted sulfonamides, by reacting these, in the presence of a catalytic amount of an organic base such as 4-dimethylaminopyridine, with activated carbonic acid esters which contain the group $-OR^2$ as the alcohol component.

The N-monosubstituted sulfonamides can be prepared according to the known methods from sulfonic acids and primary amines. To prepare the compounds of the formulae I and II with n=1, monoamines are used, to prepare the compounds of the formula I with n=2, 3 or 4, diamines, triamines or tetraamines are employed. The sulfonic acids are not used in the reaction as such, but in a more reactive, so-called "activated" form. These include, in particular, the sulfonyl halides, especially the sulfonyl chlorides.

Preferred monoamines are straight-chain or branched alkylamines having from 1 to 12, particularly preferably from 1 to 6, carbon atoms, such as methylamine, ethylamine, propylamine, isopropylamine, butylamine, sec-butylamine, isobutylamine, t-butylamine, pentylamine, 1-methylbutylamine, 2-methylbutylamine and hexylamine. Also preferred are cycloalkylamines having from 3 to 12, particularly preferably from 5 to 8, carbon atoms, such as cyclopentylamine, cyclohexylamine, cycloheptylamine and cyclooctylamine. Of the aromatic monoamines, those having from 6 to 15 carbon atoms are preferred, and their aromatic part can be substituted, especially with halogen atoms, alkyl or alkoxy groups. Examples of preferred aromatic amines are aniline, 4-methylaniline, 4-ethylaniline, 4-methoxyaniline, 3-methoxyaniline, 4-ethoxyaniline, 4-phenoxyaniline, naphthylamine, biphenylamine, 1- and 2-aminoanthracene and 9-aminophenanthrene. Among the aralkylamines, those having from 7 to 20 carbon atoms are preferred. These may be substituted in the same way as the aromatic amines. Relevant examples are benzylamine, 4-methoxybenzylamine, 2,2- and 3,3-diphenylpropylamine.

Preferred diamines are straight-chain or branched alkylenediamines having from 2 to 20 carbon atoms, which may also be substituted. In addition, individual methylene groups may also be replaced by heteroatoms, in particular oxygen. Relevant examples include ethylenediamine, propane-1,3-diamine, butane-1,3- and -1,4-diamine, pentane-1,5-diamine, hexane-1,6-diamine, 4,9-dioxadodecane-1,12-diamine and 4,7,10-trioxatridecane-1,13-diamine. Preference is also given to cycloalkylene-diamines having from 3 to 13 carbon atoms, such as cyclopentane-1,2- and -1,3-diamine, cyclohexane-1,2-, -1,3- and -1,4-diamine and methylene-bis-cyclohexane-4,4'-diyldiamine. Preferred aromatic diamines are those having from 6 to 15 carbon atoms, such as ortho-, meta- and para-phenylenediamine, 2-methyl-para-phenylenediamine, benzidine, naphthalene-1,2-, -1,3-, -1,4-, -1,5-, -2,3-, -2,4- and -2,5-diamine, anthracenediamine, acridine-3,6-diamine and phenanthrene-9,10-diamine.

An example of a tetraamine is biphenyltetraamine.

Sulfonic acids preferred for the preparation of the compounds according to the invention of the formulae I and II with n=1 are methanesulfonic acid, trifluoro-methanesulfonic acid, ethanesulfonic acid, propanesulfonic acid, perfluoropropanesulfonic acid, perfluorobutanesulfonic acid, hexanesulfonic acid, perfluorooctanesulfonic acid, benzenesulfonic acid, pentafluorobenzenesulfonic acid, para-toluenesulfonic acid and naphthalenesulfonic acid, for the preparation of compounds of the formula II, n=2, 3 or 4, in particular hexanedisulfonic acid, benzenedisulfonic acid, naphthalenedi-, -tri- and -tetrasulfonic acid, biphenyldisulfonic acid and 4,4'-oxy-bis-benzenesulfonic acid.

So-called "activated carbonic acid esters" are those which can effect acylation of the N-monosubstituted sulfonamides with —CO—OR$^2$. These are, in particular, dialkyldicarbonates (=pyrocarbonic acid dialkyl esters). Particularly preferred is di-t-butyl dicarbonate (=O[CO$_2$—C(CH$_3$)$_3$]$_2$).

The reaction of the N-monosubstituted sulfonamides with the activated carbonic acid esters is preferably carried out in a solvent which does not react irreversibly with the remaining constituents of the mixture in the presence of from about 0.01 to about 10 mol %, preferably from about 0.05 to about 2 mol %, in each case based on the molar amount of N-monosubstituted sulfonamide, of an organic base. Said base is preferably a tertiary amine, e.g. dialkylaminopyridine. Suitable solvents are, in particular, tetrahydrofuran, ethyl acetate, diethyl ether, butanone (=methyl ethyl ketone). It was found to be expedient to introduce the N-monosubstituted sulfonamide and the organic base in dissolved form as an initial charge and to slowly add to this mixture the activated carbonic acid ester. The reaction is generally carried out at a temperature of from about 0° to about 80° C., preferably from about 10° to about 50° C. The reaction product can then be isolated with sufficient purity by pouring the reaction mixture into water, filtering the precipitate and drying, or simply by stripping off the volatile constituents under reduced pressure. If required, further purification can be carried out by recrystallization, reprecipitation, distillation or by a preparative chromatographic method.

According to the invention there is further proposed a radiation-sensitive mixture which contains:

a) a compound which under the influence of actinic radiation forms acid, b) an acid-cleavable compound whose cleavage products in an aqueous-alkaline developer have a higher solubility than the starting compound, and c) a polymeric, organic binder which is insoluble in water but is soluble or at least swellable in an aqueous alkaline developer, wherein the acid-cleavable compound b) is an N,N-disubstituted sulfonamide of the formula I or II.

Suitable as compounds a) which under the influence of actinic radiation form preferably strong acids are, in particular, diazonium, phosphonium, sulfonium and iodonium salts, halogen compounds, o-quinone diazidesulfochlorides, esters and amides and also organometallic/organohalogen combinations. Said diazonium, phosphonium, sulfonium and iodonium compounds are, as a rule, employed in the form of their salts soluble in organic solvents, particularly in the form of the sulfonates, especially trifluoromethanesulfonates, of tetrafluoroborates, hexafluorophosphates, hexafluoroantimonates or hexafluoroarsenates. However, it is also possible to use halides, esters and amides of 1,2-naphthoquinone-2-diazide sulfonic acids. The acidity of the indene carboxylic acids produced upon irradiation of o-naphthoquinone diazides is, however, usually only barely adequate for sufficient imagewise differentiation. Preference is therefore given among this group to the 1,2-naphthoquinone-2-diazide-4-sulfonyl chloride, upon whose irradiation three acid functions are formed, so that a relatively large enhancement factor obtains. Finally, suitable acid formers also include organic halogen compounds; for example, those having more than one halogen atom on a carbon atom or an aromatic ring. The spectral sensitivity of said halogen-containing compounds can be modified and increased by sensitizers known per se. Examples of particularly suitable acid formers are 1,2-naphthoquinone-2-diazide-4-sulfonyl chloride; 4-di-propylaminobenzenediazonium tetrafluoroborate, hexafluorophosphate and trifluoromethanesulfonate; 2,5-diethoxy-4-p-tolylmercaptobenzenediazonium tetrafluoroborate, hexafluorophosphate and trifluoromethanesulfonate; 4-anilinobenzenediazonium sulfate and 4-diethylaminobenzenediazonium trifluoromethanesulfonate, as well as the compounds mentioned in the examples. It is also possible to use 4-methyl-6-trichloromethyl-2-pyrone; 4-(3,4,5-trimethoxystyryl)-6-trichloromethyl-2-pyrone; 4-(4-methoxystyryl)-6-(3,3,3-trichloropropenyl)-2-pyrone; 2-trichloromethylbenzimidazole; 2-tribromomethylquinolin-4-one; 2,4-dimethyl-1tribromoacetylbenzene; 3-nitro-1-tribromoacetylbenzene; 4-dibromoacetylbenzoic acid; 1,4-bis-dibromomethyl-benzene; substituted 4,6-bis-trichloromethyl-s-triazines such as 2-(6-methoxynaphthalen-2-yl)-, 2-naphthalen-1-yl-, 2-naphthalen-2-yl-, 2-[4-(2ethoxyethyl)-naphthalen-1-yl]-, 2-benzopyran-3-yl, 2-phenanthren-9-yl and 2-(4-methoxyanthrace-1-yl)-4,6-bis-trichlomethyl-s-triazine and tris-dibromomrthyl-s-triazine.

The proportion of the acid-forming component a) in the mixture can be varied depending on the composition of the mixture. Favorable results are obtained with from about 0.1 to about 20% by weight, preferably from about 0.2 to about 10% by weight, in each case based on the total weight of the solids in the mixture. Particularly in the case of copying layers having a thickness of more than 10 μm it is advisable to use relatively small amounts of acid former.

The proportion of the acid-cleavable component b) in general is from about 5 to about 50% by weight, preferably from about 10 to about 30% by weight, in each case based on the total weight of the solids in the mixture.

In addition to the acid-cleavable compounds according to the invention, others may be present in the mixture. These are, in particular, polymers having t-butoxycarbonyl groups. Mixtures having such further acid-cleavable compounds are in general not preferred, however.

Particularly suitable polymeric binders c) are phenol resins, especially cresolformaldehyde novolaks (melting range 105°–120° C. according to DIN 53181) and phenolformaldehyde novolaks (melting point 110°–120° C. according to DIN 53181).

The type and proportion of the binder depend on the application purpose. Preference is given to a proportion of t from about 30 to about 90% by weight, particularly preferably from about 55 to about 85% by weight, in each case based on the total weight of the solids in the mixture.

Binders, whose alkali solubility is increased by the action of acid, can likewise be used in the mixture according to the invention. Such binders may be, e.g., polyhydroxystyrenes whose phenolic OH groups are furnished with acid-labile groups which reduce alkali solubility. The compounds according to the invention bring about a distinct reduction of the dark ablation without adversely affecting the photosensitivity of the mixture.

Other alkali-soluble resins such as copolymers from methacrylic acid and methyl methacrylate, vinyl acetate and crotonic acid, as well as maleic anhydride and styrene are likewise suitable as binders.

In addition, numerous other resins can be used at the same time, preferably vinyl polymers such as poly(vinyl acetates), polyacrylates, poly(vinyl ethers) and poly(vinylpyrrolidones) which in turn may be modified by comonomers. The most advantageous proportion of these resins depends on the application requirements and the effect on the development conditions. In general, it is not more than about 20% by weight, based on the total weight of the binder.

In order to meet special requirements such as flexibility, adhesion or gloss, the radiation-sensitive mixture may additionally contain substances such as polyglycols, cellulose derivatives such as ethyl cellulose, wetting agents, dyes and finely dispersed pigments. Dyes which have been found to be particularly useful are the triphenylmethane dyes, especially in the form of their carbinol bases. The most advantageous quantitative ratios of the components can easily be found by experiments for each specific case.

The present invention finally also relates to a recording material comprising a base and a radiation-sensitive layer comprising the mixture according to the invention. The recording material is usually prepared by coating the base with a solution of the mixture.

Suitable solvents for the radiation-sensitive mixture according to the invention are ketones such as methyl ethyl ketone, chlorinated hydrocarbons such as trichloro-ethylene and 1,1,1-trichloroethane, alcohols such as n-propanol, ethers such as tetrahydrofuran, glycol ethers such as ethylene glycol monoethyl ether, and esters such as butyl acetate. It is also possible to use mixtures which, moreover, for special purposes may additionally contain solvents such as acetonitrile, dioxane or dimethylformamide. In principle, all solvents can be used which do not react irreversibly with the layer components. They should, however, be selected with regard to the coating process intended, the layer thickness and the drying appliance. Thin layers up to approximately 5 μm in experimental amounts are preferably applied by spin-coating. Layer thicknesses of more than 60 μm can be achieved with solutions of up to approximately 40% solids content by a single application to the spinning disc or using a doctor knife. Bilateral coating is preferably effected by dip-coating, rapid surface drying being advantageous and being achieved by employing low-boiling solvents. Strip-shaped base materials can be coated by spraying the coating solution using sheet dies or by application using rollers; individual plates, such as zinc and multimetal plates, can be coated by curtain coating.

Compared to other positive layers, especially those based on o-naphthoquinone diazide, it is also possible to produce thicker layers, as the photosensitivity of the mixtures according to the invention varies comparatively little with thickness.

Exposure and processing of layers having a thickness of 100 μm and more is possible.

Preferred bases for layers having a thickness of more than 10 μm are plastic sheets which then serve as temporary bases for transfer layers. For this purpose and for color sheets, polyester sheets are preferred, e.g. from polyethylene terephthalate. Polyolefin sheets such as polypropylene are likewise suitable, however. If layer thicknesses are less than 10 μm, the film bases employed are usually metals. Offset printing plates can be manufactured by employing mechanically or electrochemically roughened and optionally anodized aluminum, which may be pretreated chemically (e.g. with polyvinylphosphonic acid, silicates or phosphates). Also suitable are multi-metal plates having Cu/Cr or brass/Cr as the uppermost layer. To prepare relief printing plates, the layers according to the invention can be applied to zinc or magnesium plates or their commercial microcrystalline alloys for powderless etching, also to etchable plastics such as polyoxymethylene. For the purpose of rotogravure or halftone formes these layers are suitable owing to their good adhesion and etch resistance on copper or nickel surfaces. Similarly, they can be used as photoresists and in chemical milling.

Finally, coating can be effected directly or by dry layer transfer from the temporary base to printed-circuit board materials comprising insulating plates coated with copper on one side or both sides, onto glass or ceramic materials which may, if appropriate, have been pretreated to promote adhesion, and, inter alia, to silicon wafers on whose surface there may be, if appropriate, a nitride or oxide layer. In addition, it is possible to coat wood, textiles and surfaces of many materials which are preferably illustrated by a projection and are resistant to the influence of alkaline developers.

The coating can be dried with the usual equipment, employing the usual conditions. It withstands temperatures around 100° C., on a short-term basis even as high as 120° C., without a loss in radiation sensitivity being observed subsequently.

Irradiation can be carried out employing the usual radiation sources, such as tubular lamps, pulsed xenon discharge lamps, metal halide-doped high-pressure mercury vapor lamps and carbon arc lamps. In addition, it is possible to irradiate in conventional projection and enlargement equipment under the light of metal filament lamps, or contact exposure using ordinary light bulbs is possible. Irradiation can alternately be effected with the coherent light of a laser. Suitable for this purpose are high-power short-wavelength lasers, for example argon ion lasers, krypton ion lasers, dye lasers, helium-cadmium lasers and excimer lasers emitting between 193 and 633 nm. The laser is usually passed over the recording layer under computer control in a raster-or stroke-like manner and in the process irradiates the latter imagewise.

Irradiation with electron beams forms a further illustration possibility. Electron beams are able to decompose thoroughly and then crosslink the mixture according to the invention, like many other organic materials, so that a negative image is produced if the non-irradiated regions are removed by solvents or exposure without a pattern and development. If the intensity of the electron beam is lower, and/or the writing speed thereof is higher, the electron beam, in contrast, has a differentiating effect in the direction of higher solubility, i.e. the irradiated layer portions can be removed by the developer. The most favorable conditions to be chosen are easily determined by experiments.

The layer, after imagewise exposure or irradiation, can be removed, after thermal secondary treatment if required, using virtually the same developers as for commercially available naphthoquinone diazide layers and photoresists, and the novel layers, as far as their copying conditions are concerned, can be advantageously tailored to the conventional aids such as developers and programmed spray development equipment. The aqueous developer solutions may contain, e.g., alkali metal phosphates, silicates or hydroxides and also wetting agents as well as minor proportions of organic solvents. In certain cases it is possible to use, instead of the aqueous alkaline developers, organic solvents or mixtures of organic solvents with water as the developer. The preferred developers, however, are aqueous alkaline solutions.

The most advantageous developer can be determined by experiments with the layer in a particular case. If required, development can be assisted mechanically. So as to increase the robustness during printing and the resistance against leaching agents, correcting agents and inks curable by UV light, the developed plates may be heated to elevated temperatures for a short time.

Hereinafter, examples are given of the preferred N,N-disubstituted sulfonamides according to the invention, their synthesis and the preferred photosensitive mixtures obtainable by employing these without restricting the invention thereto. In the examples, ppw represents parts by weight.

EXAMPLES 1 to 18

1 mol of N-substituted sulfonamide and 0.02 mol of 4-dimethylaminopyridine are dissolved in 700 ml of ethyl acetate or tetrahydrofuran. At room temperature, a solution of n mol of di-t-butyldicarbonate in 300 ml of ethyl acetate or tetrahydrofuran is added dropwise over 30 min to the stirred solution. After the reaction is complete, the product is isolated by stripping off the solvent under reduced pressure or by pouring the reaction solution into water, filtering off the product thus precipitated with suction, and drying. According to this method, the N,N-disubstituted sulfonamides listed in Table 1 are obtained.

TABLE 1

| | | N,N-disubstituted sulfonamides according to the invention | | | | |
|---|---|---|---|---|---|---|
| Ex. | Formula | $R^1$ | $R^2$ | $R^3$ | n | mp (°C.) |
| 1 | I | Methyl | t-Bu | p-Tolyl | 1 | 72–73 |
| 2 | I | n-Propyl | t-Bu | p-Tolyl | 1 | 43–44 |
| 3 | I | n-Butyl | t-Bu | p-Tolyl | 1 | 51–52 |
| 4 | I | Phenyl | t-Bu | p-Tolyl | 1 | 122–123 |
| 5 | I | Phenyl | t-Bu | Methyl | 1 | 109–110 |
| 6 | I | Phenyl | t-Bu | 2-Naphthyl | 1 | 152–153 |
| 7 | I | Phenyl | t-Bu | 1-Naphthyl | 1 | 82–83 |
| 8 | II | Biphenyl-4,4'-diyl | t-Bu | n-Propyl | 2 | 153–154 |
| 9 | II | Naphthalene-1,5-diyl | t-Bu | Phenyl | 2 | 251–252 |
| 10 | II | Biphenyl-4,4'-diyl | t-Bu | Phenyl | 2 | 223–224 |
| 11 | II | Oxybiphenyl-4,4'-diyl | t-Bu | Benzyl | 2 | 131–132 |
| 12 | II | Biphenyl-4,4'-diyl | t-Bu | Benzyl | 2 | 246–249 |
| 13 | I | Butane-1,4-diyl | t-Bu | p-Tolyl | 2 | 132–133 |
| 14 | I | p-Phenylene | t-Bu | p-Tolyl | 2 | 277–278 |

TABLE 1-continued

| | | N,N-disubstituted sulfonamides according to the invention | | | | |
|---|---|---|---|---|---|---|
| Ex. | Formula | $R^1$ | $R^2$ | $R^3$ | n | mp (°C.) |
| 15 | I | Oxybiphenyl-4,4'-diyl | t-Bu | p-Tolyl | 2 | 163 |
| 16 | I | 4,9-Dioxadodecane-1,12-diyl | t-Bu | p-Tolyl | 2 | 84–85 |
| 17 | I | 4,7,10-Trioxatridecane-1,13-diyl | t-Bu | p-Tolyl | 2 | oil |
| 18 | I | Methylene-bis-cyclohexane-4,4'-diyl | t-Bu | p-Tolyl | 2 | 174–175 |

EXAMPLE 19

A coating solution comprising 6.50 ppw of novolak, 2.50 ppw of, in each case, one of the N,N-disubstituted sulfonamides listed in Table 1, 0.50 ppw of 4-p-tolylmercapto-2,5-diethoxybenzenediazonium hexafluorophosphate, 0.08 ppw of crystal violet base and 175 ppw of methyl ethyl ketone is spin-coated onto plates of electrochemically activated and anodized aluminum and dried at 100° C. in the drying oven, the layer thickness after drying being from 1.8 to 2.0 µm. The plates are irradiated with a 5 kW metal halide lamp at a distance of 110 cm above the radiation-sensitive layer through a halftone step wedge having 13 steps with a density gradation of 0.15, is then heated in a drying oven for 1 min at 100° C. and developed in an aqueous alkaline developer having the composition 5.5 ppw of sodium metasilicate –9 $H_2O$ 3.4 ppw of trisodium phosphate –12 $H_2O$, 0.4 ppw of monosodiumphosphate anhydrous and 90.7 ppw of deionized water.

Satisfactory, positive images of the photographic master are obtained. When compounds 8, 9, 12 or 16 are employed, the quality of the images was somewhat poorer.

EXAMPLES 20 to 27

A plate of electrochemically activated and anodized aluminum is spin-coated with a solution comprising:

6.50 ppw of binder (BM), 2.50 ppw of N,N-disubstituted sulfonamide, 0.50 ppw of 4-p-tolylmercapto-2,5-diethoxybenzenediazonium hexafluorophosphate, 0.08 ppw of crystal violet base and 175 ppw of methyl ethyl ketone and heated at 100° C. in a drying oven, resulting in a layer thickness of 1.9 µm. The plate is exposed under a 5 kW metal halide lamp at a distance of 110 cm through a halftone step wedge having 13 steps with a density gradation of 0.15, is then heated for 1 min at 100° C. and developed for 30 s in an aqueous alkaline developer of the composition specified in Example 19. In all cases, a positive image of the photographic master is obtained. Table 2 further indicates at what exposure time step 4 of the halftone wedge is reproduced as open on the plate and thus shows the distinctly higher photosensitivity of the photosensitive layers according to the invention compared to known photoresists.

TABLE 2

| Example | Sulfonamide according to Table 1 | Exposure time in s | Binder |
|---|---|---|---|
| 20 | 2 | 40 | Novolak |
| 21 | 4 | 40 | Novolak |
| 22 | 6 | 55 | Novolak |
| 23 | 6 | 40 | Poly-3-methyl-p-hydroxystyrene |
| 24 | 1 | 45 | Copolymer from pyrocatechol mono-methacrylate and styrene Novolak |
| 25 | 7 | 65 | Novolak |
| 26 | | 40 | Novolak |
| 27 | 17 | 30 | Novolak |
| Cmp.* | 1 | 75 | — |

*An offset printing plate ® Ozasol P 61 (Hoechst AG) was used

EXAMPLE 28

This example shows the suitability of the mixtures according to the invention for preparing positive offset printing plates.

A plate of electrochemically activated and anodized aluminum is spin-coated with a solution comprising:

7.00 ppw of novolak, 2.00 ppw of N-t-butoxycarbonyl-N-phenyl-naphthalene-2-sulfonamide (Example 6 in Table 1), 0.50 ppw of 4-p-tolylmercapto-2,5-diethoxybenzenediazonium hexafluorophosphate, 0.08 ppw of crystal violet base and 175 ppw of methyl ethyl ketone and heated at 100° C. in a drying oven, resulting in a layer thickness of 1.9 µm. The plate is exposed for 30 s under a 5 kW metal halide lamp at a distance of 110 cm through a halftone step wedge having 13 steps with a density gradation of 0.15, is then heated for 1 min at 100° C. and developed for 30 seconds in an aqueous alkaline developer of the composition specified in Example 19. The positive printing forme thus obtained produces more than 90,000 good-quality prints on an offset printing machine.

EXAMPLES 29 to 32

These examples show the reduction of dark ablation of copying layers while maintaining unchanged photosensitivity, as a result of the addition of the compounds according to the invention.

Plates of electrochemically activated and anodized aluminum are spin-coated with a solution comprising:

8.00 ppw of binder, obtained by reacting 2 ppw of polyhydroxystyrene (MW 4500) with 1 ppw of di-t-butyl dicarbonate, 1.00 ppw of N,N-disubstituted sulfonamide, 0.50 ppw of acid donor 2,5-diethoxy-4-(p-tolylmercapto)-benzenediazonium hexafluorophosphate, 0.08 ppw of crystal violet base and 175 ppw of methyl ethyl ketone and heated at 100° C. in a circulating drying oven, resulting in a layer thicknesses of 1.9 µm. The plates were exposed under a 5 kW metal halide lamp at a distance of 110 cm through a halftone step wedge having 13 steps with a density gradation of 0.15, are then heated for 1 min at 100° C. and developed in an aqueous alkaline developer of the composition specified in Example 19, the plates remaining in the developer for 30 seconds on one occasion, but for 270 seconds on another occasion. The results are shown by Table 3.

TABLE 3

Reduction of the dark ablation of copying layers by the compounds according to the invention

| Ex. | Sulfonamide according to Table 1 | Open halftone wedge step | | Lines in µ | |
|---|---|---|---|---|---|
| | | 30 s | 270 s | 30 s | 270 s |
| 29 | 1 | 3 | 5 | 15 | 20 |
| 30 | 4 | 3 | 4 | 15 | 20 |
| 31 | 2 | 3 | 5 | 15 | 20 |
| 32 | 3 | 3 | 5 | 15 | 20 |
| Cmp.* | — | 3 | 6 | 15 | 20 |

*In this layer (reference layer), the proportion of compound according to the invention has been replaced by a correspondingly higher proportion of binder.

We claim:

1. A radiation-sensitive mixture which comprises:

a) a compound which under the influence of actinic radiation forms acid, b) an acid-cleavable compound whose cleavage products in an aqueous-alkaline developer have a higher solubility than the starting compound, and c) a polymeric organic binder which is insoluble in water but is soluble or at least swellable in an aqueous alkaline developer, wherein the acid-cleavable compound b) is an N,N-disubstituted sulfonamide of the formulae $R^1[-N(CO-OR^2)-SO_2-R^3]_n$ (I) or $R^1[-SO_2-N(CO-OR^2)-R^3]_n$ (II) in which $R^1$ for n=1 is a $(C_1-C_{20})$alkyl, $(C_3-C_{10})$cycloalkyl, $(C_6-C_{14})$aryl or $(C_7-C_{20})$aralkyl radical, individual methylene groups in the radicals containing alkyl being optionally replaced by oxygen for n=2, 3 or 4 the n-valent radical of a $(C_1-C_{20})$alkane or $(C_5-C_7)$cycloalkane, individual methylene groups in the n-valent $(C_3-C_{20})$alkane groups being optionally replaced by oxygen, by $(C_5-C_7)$cycloaklylene radicals or by phenylene, or the n-valent radical of a non-condensed or condensed polynuclear $(C_6-C_{18})$aromatic compound or a mononuclear $(C_6-C_{18})$aromatic compound, $R^2$ is a $(C_3-C_{11})$alkyl, $(C_3-C_{11})$alkenyl or $(C_7-C_{11})$aralkyl radical, $R^3$ is a $(C_1-C_6)$alkyl, $(C_3-C_6)$cycloalkyl, $(C_6-C_{14})$aryl or $(C_7-C_{20})$aralkyl radical, and n is an integer from 1 to 4.

2. The radiation-sensitive mixture as claimed in claim 1, wherein the proportion of the acid-forming compound(s) a) is from about 0.1 to about 20% by weight based on the total weight of the solids in the mixture.

3. The radiation-sensitive mixture as claimed in claim 2, wherein the proportion of the acid-forming compound(s) a) is from about 0.2 to about 10% by weight based on the total weight of the solids in the mixture.

4. The radiation-sensitive mixture as claimed in claim 1, wherein the proportion of the acid-cleavable compound(s) b) is from about 5 to about 50% by weight based on the total weight of the solids in the mixture.

5. The radiation-sensitive mixture as claimed in claim 4, wherein the proportion of the acid-cleavable compound(s) b) is from about 10 to about 30% by weight based on the total weight of the solids in the mixture.

6. The radiation-sensitive mixture as claimed in claim 1, wherein the proportion of the polymeric binder c) is from about 30 to about 90% by weight based on the total weight of the solids in the mixture.

7. The radiation-sensitive mixture as claimed in claim 6, wherein the proportion of the polymeric binder c) is from about 55 to about 85% by weight based on the total weight of the solids in the mixture.

8. A recording material comprising a base and a radiation-sensitive layer comprising:
   a) a compound which under the influence of actinic radiation forms acid,
   b) an acid-cleavable compound whose cleavage products in an aqueous-alkaline developer have a higher solubility than the starting compound, and
   c) a polymeric organic binder which is insoluble in water but is soluble or at least swellable in an aqueous alkaline developer, wherein the acid-cleavable compound b) is an N,N-disubstituted sulfonamide of the formulae $R^1[-N(CO-OR^2)-SO_2-R^3]_n$ (I) or $R^1[-SO_2-N(CO-OR^2)-R^3]_n$ (II) in which $R^1$ for n=1 is a $(C_1-C_{20})$alkyl, $(C_3-C_{10})$cycloalkyl, $(C_6-C_{14})$aryl or $(C_7-C_{20})$aralkyl radical, individual methylene groups in the radicals containing alkyl being optionally replaced by oxygen, for n=2, 3 or 4 the n-valent radical of a $(C_1-C_{20})$alkane or $(C_5-C_7)$cycloalkane, individual methylene groups in the n-valent $(C_3-C_{20})$alkane groups being optionally replaced by oxygen, by $(C_5-C_7)$cycloalkylene radicals or by phenylene, or the n-valent radical of a non-condensed or condensed polynuclear $(C_6-C_{18})$aromatic compound or a mononuclear $(C_6-C_{18})$aromatic compound, $R^2$ is a $(C_3-C_{11})$alkyl, $(C_3-C_{11})$alkenyl or $(C_7-C_{11})$aralkyl radical, $R^3$ is a $(C_1-C_6)$alkyl, $(C_3-C_6)$cycloalkyl, $(C_6-C_{14})$aryl or $(C_7-C_{20})$aralkyl radical, and n is an integer from 1 to 4.

* * * * *